United States Patent [19]
Righetto et al.

[11] Patent Number: 5,856,299
[45] Date of Patent: Jan. 5, 1999

[54] HIGHLY REACTIVE ESTERS OF CARBOXY POLYSACCHARIDES AND CARBOXY POLYSACCHARIDES DERIVED THEREFROM

[75] Inventors: Zefferino Righetto, Camponogara; Davide Bellini, Montegrotto Terme, both of Italy

[73] Assignee: Fidia Advanced Biopolymers S.r.l., Brindisi, Italy

[21] Appl. No.: 702,673

[22] PCT Filed: Mar. 13, 1995

[86] PCT No.: PCT/EP95/00932

§ 371 Date: Nov. 26, 1996

§ 102(e) Date: Nov. 26, 1996

[87] PCT Pub. No.: WO95/24429

PCT Pub. Date: Sep. 14, 1995

[30] Foreign Application Priority Data

Mar. 11, 1994 [IT] Italy ................................. PD94A0043

[51] Int. Cl.$^6$ .......................... C07H 13/00; A61K 31/215
[52] U.S. Cl. .................. 514/8; 514/23; 514/26; 514/54; 514/178; 514/181; 514/453; 536/3; 536/18.7; 536/55.1; 536/53; 536/115; 536/119
[58] Field of Search .................... 514/8, 23, 26, 514/54, 178, 181, 453; 536/3, 18.7, 55.1, 53, 115, 119; 424/40, 423, 408, 422

[56] References Cited

U.S. PATENT DOCUMENTS

| | | | |
|---|---|---|---|
| 5,122,598 | 6/1992 | Della Valle et al. | 536/20 |
| 5,202,431 | 4/1993 | Della Valle et al. | 536/55.1 |
| 5,332,809 | 7/1994 | Della Valle et al. | 536/119 |
| 5,336,668 | 8/1994 | Della Valle et al. | 514/23 |
| 5,676,964 | 10/1997 | Della Valle et al. | 424/423 |

FOREIGN PATENT DOCUMENTS 9220349   10/1992   WIPO .

*Primary Examiner*—Cecilia J. Tsang
*Assistant Examiner*—Bennett Celsa
*Attorney, Agent, or Firm*—Birch, Stewart, Kolasch & Birch, LLP

[57] ABSTRACT

Provided are active esters of carboxy polysaccharides and semisynthetic derivatives of carboxy polysaccharides, wherein all or part of the carboxy groups thereof are esterified with an aromatic alcohol, a substituted aromatic alcohol, an aromatic heterocyclic alcohol, a substituted aromatic heterocyclic alcohol, an N-hydroxylamine, or a combination thereof. Also provided is a process for producing such active esters. These active esters can be used for the preparation of modified carboxy polysaccharides or modified semisynthetic derivatives of such carboxy polysaccharides, in the form of esters, thioesters, or amides. Such active esters, modified polysaccharides, and modified semisynthetic derivatives of carboxy polysaccharides can be used in the biomedical and pharmaceutical fields to prepare, for example, cosmetic articles, health care articles, surgical articles, and diagnostic kits.

32 Claims, No Drawings

5,856,299

HIGHLY REACTIVE ESTERS OF CARBOXY POLYSACCHARIDES AND CARBOXY POLYSACCHARIDES DERIVED THEREFROM

BACKGROUND OF THE INVENTION

1. Field of the Invention

The present invention relates to active esters of carboxy polysaccharides and semisynthetic derivatives of such carboxy polysaccharides, wherein all or a part of the carboxy functions of the polysaccharides are esterified with alcohols of the aromatic, heterocyclic aromatic, or N-hydroxylamine series and, in the case of active partial esters, the remaining carboxy functions are salified with quaternary ammonium salts or metals. The present invention also relates to a method for the synthesis of said active esters starting with carboxy polysaccharides and their semisynthetic derivatives.

The present invention also relates to the use of such active esters as intermediates in the synthesis of modified carboxy polysaccharides and modified semisynthetic derivatives of carboxy polysaccharides, the modified polysaccharides and modified semisynthetic derivatives thereof per se, and the use of such modified polysaccharides and semisynthetic derivatives thereof to produce health care and surgical articles for use in the pharmaceutical and biomedical fields.

DESCRIPTION OF RELATED ART

There are reports in the literature of methods for for the synthesis and appliation of active esters for amino acids which comprise stable intermediates for use in the synthesis of peptides (see Fields, C. B. and Noble, R. L. (1990) *Int. J. Peptide Protein Res.* 35:613–214; Atherton, E. and Sheppard, R. C. (1989) in *Solid Phase Peptide Synthesis, A Practical Approach,* IRL Press, Oxford; M. Bodansky (1984) in *Principles of Peptide Synthesis,* Springer-Verlag, Berlin, Heidelberg). Said esters result in greater reactivity of the carboxy group in nucleophilic substitution reactions as the strongly electron-attracting group bound to the carbonyl carbon can be easily substituted with a nucleophile (sulfide, amine, alcoholic hydroxyl) to produce thioesters, amides, and esters under suitable reaction conditions, i.e., solvents, temperature, catalysts, etc. Esters with aromatic, substituted aromatic, aromatic heterocyclic, and substituted aromatic heterocyclic alcohols, and N-hydroxylamines, belong to this class of active esters.

International patent application WO-A-92/20349 discloses water insoluble biocompatible compositions. The compositions of WO-A-92//20349 are made by mixing in a "one-pot" reaction a polyanionic polysaccharide, an activating agent, a modifying agent and a nucleophile. The reactions of WO-A-92/20349 are done in a single reaction vessel; and because of the reaction conditions used, it is not possible to isolate any intermediates.

SUMMARY OF THE INVENTION

The present invention provides a novel method for producing esters, amides, and thioesters of carboxy polysaccharides via the formation of active ester intermediates, and subsequent nucleophilic substitution at the carboxyl functions of the polysaccharides.

Apart from being used as intermediate products which are stable and easily stored, due to subsequent nucleophile substitution reactions, the active esters of carboxy polysaccharides and their semisynthetic derivatives can be used as reaction intermediates for the preparation of diagnostic kits as surfaces for the activation of proteins.

The production method is mainly based upon plasmacoating applied between the polymeric surface of the support, e.g., polystyrene, and the activated polysaccharide with the formation of stable bonds.

According to the intended diagnostic use, the activated polysaccharide-based surface is treated with a polypeptide or protein that binds to the polysaccharide by a nucleophilic substitution reaction. The treated material can therefore be used (a) to identify biochemical targets, such as antibodies or other polypeptides compatible with the molecules bound to the hyaluronic acid by spectrophotometry or immunological methods (ELISA), and (b) to coat laboratory equipment and dishes for the cultivation and regeneration of cells and tissues.

For example, the typical hydrophilic characteristics of hyaluronic acid, in association with suitable polymeric supports, make the active esters with varying degrees of substitution useful in the biomedical field for any use which requires the blocking on the surface of the support of proteins or peptides which must then be detected and quantified by spectrophotometry or immunoenzymatic methods.

Hyaluronic acid amides are useful for two distinct purposes:

a) the slow, controlled release of natural hyaluronic acid as a result of the greater stability of the amide bond compared to the ester bond; and b) the controlled release of the substituting group, the biological activity of which depends upon its nature.

The carboxy polysaccharides and semisynthetic derivatives thereof employed in the present invention are all known and described, for example, in U.S. Pat. Nos. 4,851, 521, 5,122,598, 5,300,493, 5,332,809, and 5,336,668; European Patent Application No. 93917681.4; EP 0 216 453, EP 0 251 905, EP 0 342 557, EP 0 518 710, EP 0 603 264, and EP 0 605 478; and WO 93/06136 and WO 94/03499. Among these are glycosaminoglycans, alginic acid, gellan, carboxymethylcellulose, carboxymethylchitin, and carboxymethylamide. Of particular importance among the glycosaminoglycans is hyaluronic acid. Of the semisynthetic derivatives of polysaccharides, salts thereof, especially quaternary ammonium salts, are particularly important. Other important semisynthetic derivatives useful in the present invention are the partial esters of carboxy polysaccharides with aliphatic, araliphatic, heterocyclic and cycloaliphatic alcohols.

The methods of synthesis and applications of quaternary ammonium salts, in particular tetrabutylammonium salts, and carboxy polysaccharide esters with aliphatic, araliphatic, heterocyclic and cycloaliphatic alcohols, are described in the patent publications listed supra.

The stability and versatility of the present active esters of carboxy polysaccharides make these compounds useful in the synthesis of a variety of modified polysaccharides, in particular amide derivatives of such polysaccharides. Among such polysaccharide derivatives, those obtained by reaction of active esters with primary amines, amino acids, peptides, and proteins are particularly important.

Accordingly, it is an object of the present invention to provide an active ester of a carboxy polysaccharide or a semisynthetic derivative of a carboxy polysaccharide, wherein all or part of the carboxy groups thereof are esterified with an alcohol selected from the group consisting of an aromatic alcohol, a substituted aromatic alcohol, an aromatic heterocyclic alcohol, a substituted aromatic heterocyclic alcohol, an N-hydroxylamine, and a combination thereof, wherein when only part of the carboxy groups of said carboxy polysaccharide or said semisynthetic derivative of said carboxy polysaccharide are esterified, the remaining carboxy groups are salified with a member selected from the group consisting of a quaternary ammonium salt, an alkaline metal, an alkaline earth metal, and a combination thereof.

Another object of the present invention is to provide a process for producing an active ester as described above, comprising reacting a tetraalkylammonium salt of a carboxy polysaccharide or a semisynthetic derivative of a carboxy polysaccharide with a reactive derivative of an alcohol to be bound to the carboxyl groups thereof in an aprotic solvent at a temperature of between about 0° and about 60° C.

Another object of the present invention is the use of such active esters for the preparation of a modified carboxy polysaccharide or a modified semisynthetic derivative of a carboxy polysaccharide, wherein said modified carboxy polysaccharide or said modified semisynthetic derivative of a carboxy polysaccharide is an ester, thioester, or amide.

A further object of the present invention is a modified carboxy polysaccharide, or a modified semisynthetic derivative of a carboxy polysaccharide, prepared from such active esters.

A still further object of the present invention is the use of such active esters, modified polysaccharides, and modified semisynthetic derivatives of such polysaccharides in the biomedical and pharmaceutical fields to prepare, for example, cosmetic articles, health care articles, surgical articles, and diagnostic kits.

Further scope of the applicability of the present invention will become apparent from the detailed description provided below. It should be understood, however, that the following detailed description and specific examples, while indicating preferred embodiments of the present invention, are given by way of illustration only since various changes and modifications within the spirit and scope of the present invention will become apparent to those skilled in the art from this detailed description.

DETAILED DESCRIPTION OF THE INVENTION

The following detailed description of the present invention is provided to aid those skilled in the art in practicing the same. Even so, the following detailed description should not be construed to unduly limit the present invention, as modifications and variations in the embodiments discussed herein may be made by those of ordinary skill in the art without departing from the spirit or scope of the present inventive discovery.

The contents of each of the references discussed herein are herein incorporated by reference in their entirety.

Alcohols Useful In Preparing Active Carboxy Polysaccharide Esters

The active esters of carboxy polysaccharides and semisynthetic derivatives thereof of the present invention are those with alcohols of the aromatic, substituted aromatic, aromatic heterocyclic, substituted aromatic heterocyclic, and N-hydroxyl amine type.

These alcohols include, but are not limited to:
pentafluorophenol, pentachlorophenol, trichlorophenol, p-nitrophenol, 2,4-dinitrophenol, 2-hydroxypyridine, 3-hydroxypyridine, 3,4-dihydro-4-oxobenzotriazine-3-ol, 4-hydroxy-2,5-diphenyl-3(2H)-thiophenone-1, 1-dioxide, 3-phenyl-1-(p-nitrophenyl)-2-pyrazoline-5-one, 3-methyl-1-(p-nitrophenyl)-2-pyrazoline-5-one, N-hydroxysuccinimide, and N-hydroxyphthalimide.

Esters

The most interesting of the esters that can be obtained include the p-nitrophenyl ester, the pentafluorophenyl ester, the 4-dihydro-4-oxobenzotriazine-3-yl ester, and the N-succinimidyl ester.

The active esters can be total, i.e., all the carboxy functions of the polysaccharide are employed in the formation of the active ester, or partial, i.e., only part of the carboxy functions are involved in the formation of the active ester.

In the case of partial active esters, the carboxy functions not involved in the formation of the active ester are in the form of a salt, in particular the tetrabutylammonium salt. Formation of active esters of semisynthetic derivatives of carboxy polysaccharides involves reaction at the carboxyl groups not already covalently bound therein.

Carboxy Polysaccharides

The carboxy polysaccharides that can be employed as substrates for the synthesis of active esters are those already known and described, including naturally occurring polysaccharides of animal or vegetable origin, and semisynthetic derivatives thereof. Particularly useful carboxy polysaccharides include, but are not limited to, glycosaminoglycans, e.g., hyaluronic acid, as well as alginic acid, gellan, carboxymethylcellulose, carboxymethylchitin, and carboxymethyl amide.

Of the semisynthetic derivatives, carboxy polysaccharide salts, in particular quaternary ammonium salts such as tetraalkyl ammonium salts, for example, tetrabutylammonium salt, is preferred.

As semisynthetic carboxy polysaccharide starting materials, it is also possible to use partial esters of said polysaccharides, in particular esters with alcohols of the aliphatic, araliphatic, cycloaliphatic, and heterocyclic series. Of these, the partial esters with aliphatic alcohols having between 2 and 34 carbon atoms, in particular ethanol, and partial esters with alcohols of the araliphatic series, in particular benzyl alcohol, are preferred. The partial esters of hyaluronic acid known as HYAFF, described in U.S. Pat. Nos. 4,851,521, 4,965,353, and 5,202,431, typify such partial esters.

Surprisingly, active esters of carboxy polysaccharides and their semisynthetic derivatives have been obtained without any undesired side reactions, such as the formation of intra- and inter-chain bridges, which lead to the phenomenon known as auto-crosslinking.

Reaction Conditions

The formation reaction of the active esters starting from carboxy polysaccharides or semisynthetic derivatives thereof, wherein all or part of the carboxy functions are salified with a tetraalkylammonium salt, occurs by first-order kinetics.

Activation of the carbonyl residues is achieved by classic stoichiometric methods, and the percentage of active ester formed depends upon the quantity (in mEq) of alcohol or N-hydroxylamine added to the carboxy polysaccharide tetrabutylammonium salt. Temperature does not seem to be a significant determinant factor in the esterification yield.

The reaction is conducted by adding the esterification reagent to a solution of the carboxy polysaccharide which is in the form of a tetraalkylammonium, e.g., tetrabutylammonium, salt, or to a solution of the partial carboxy polysaccharide ester, in which case the remaining carboxy functions are in the form of tetraalkyl, e.g., tetrabutylammonium, salts, in an aprotic solvent such as dimethylsulfoxide, N-methylpyrrolidone, or N,N'-dimethylformamide. The reaction temperature can be in the range of from about 0° C. to about 60° C., preferably about 25° C. to about 40° C., depending upon the reagent used.

Reactive Derivatives

The reactive derivatives that can be used for the synthesis of the active esters are aryl trifluoroacetates, such as p-nitrophenyl trifluoroacetate and pentafluorophenyl trifluoroacetate; aryl phosphites; aryl sulfites, such as di-pentafluorophenyl sulfite; carbonates, such as di-(N-succinimidyl)carbonate and 4,6-diphenylthiene-[3,4-d]-1,3-dioxol-2-one5,5-dioxide (TDO carbonate, or Steglich's reagent).

New Carboxy Polysaccharide Derivatives Derived From Active Esters

The resulting active carboxy polyssacharide esters can be advantageously employed in the synthesis of new carboxy polysaccharide derivatives as these active esters exhibit high reactivity in nucleophilic substitution reactions at the carbonyl carbons of activated carboxyl groups.

Nucleophiles

Nucleophiles that can be used in such reactions include, but are not limited to, primary amines, amino acids, peptides, proteins, mercaptans, and alcohols.

Useful primary amines include aliphatic amines, araliphatic amines, and substituted derivatives of said amines, such as aliphatic amines containing alkyl chains substituted with halogen atoms, in particular perfluoroamines.

Among the useful primary amines are ethylamine, n-propylamine, isopropylamine, N-butylamine, N-heptylamine, benzylamine, N-ethyl aminobenzene, benzedrine, benzocaine, and N-pentylamine.

The amino acids that can be employed include all known amino acids, and the same is true of peptides and proteins.

Among the amino acids that can be particularly mentioned are phenylalanine, glycine, serine, leucine, tryptophan, aspartic acid, arginine, and serine benzyl ester.

Among the polypeptides are Phe-Val-Glu-Tyr-Leu (SEQ ID NO:1), Gly-Arg-Gly-Asp-Ser-Tyr (SEQ ID NO:2), Gly-Arg-Gly-Asp-Val-Tyr (SEQ ID NO:3), and Gly-Arg-Gly-Glu-Ser-Tyr (SEQ ID NO:4).

Among the proteins are albumin and calcitonin.

Among the mercaptans are thioethane, thiofuran, thiophenol, thioanisol, thioglycerol, and 5-thioglucose.

Useful alcohols include those disclosed in U.S. Pat. Nos. 4,851,521, 4,965,353, and 5,202,431. These patents also disclose other primary amines, amino acids, peptides, proteins, and mercaptans useful in the present invention.

Properties of the active esters of carboxy polysaccharides and their semisynthetic derivatives that are extremely useful include their high reactivity and selectivity with respect to amines compared to that with alcohols and mercaptans in nucleophilic substitution reactions. This leads to a significant decrease in undesirable secondary reactions in the synthesis of new, modified polysaccharides, which occur, for example, when condensing agents such as dicyclohexylcarbodiimide, N-hydroxy-benzotriazol, etc., are employed, or due to the presence of functional groups such as amino or hydroxy groups, for example.

The new modified polysaccharides produced from active esters of the present invention can be used in the preparation of health care and surgical articles for internal or external use, such as microcapsules, microspheres, threads, films, gauzes, sponges, etc., as described in U.S. Pat. Nos. 4,851,521, 4,965,353, and 5,202,431. These can be advantageously employed in the biomedical and pharmaceutical fields such as, for example, in the areas of wound care, tissue healing and repair, prevention of tissue adhesion, and in controlled-release systems for biologically active substances such as amino acids, peptides, and proteins.

While the Examples presented below describe the formation of various derivatives of hyaluronic acid, the same methods can be employed with the other carboxy polysaccharides of the present invention, such as alginic acid, gellan, carboxymethylcellulose, carboxymethylchitin, carboxymethylamide, etc.

EXAMPLE 1

Preparation of a pentafluorophenyl partial ester of hyaluronic acid tetrabutylammonium salt —5% of the carboxy groups are involved in the formation of the active ester—95% of the carboxy groups are in the form of tetrabutylammonium salt 6.2 grams of hyaluronic acid tetrabutylammonium salt with a molecular weight of 180,000 Daltons, corresponding to 10 mEq of a monomeric unit, are solubilized in 310 ml of N-methylpyrrolidone at 25° C. This solution is shaken while 0.040 ml of pyridine (0.5 mEq) are added, followed by 0.088 ml of pentafluorophenyl trifluoroacetate (0.5 mEq). The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

6.15 grams of product with the desired titer are thus obtained. Quantitative analysis of the percentage of esterification was performed by gas chromatography to determine the pentafluorophenol content after alkaline hydrolysis of the ester.

EXAMPLE 2

Preparation of a pentafluorophenyl partial ester of hyaluronic acid tetrabutylammonium salt —10% of the carboxy groups are involved in the formation of the active ester—90% of the carboxy groups are in the form of tetrabutylammonium salt 6.2 grams of hyaluronic acid tetrabutylammonium salt with a molecular weight of 160,000 Daltons, corresponding to 10 mEq of a monomeric unit, are solubilized in 310 ml of N-methylpyrrolidone at 25° C. This solution is shaken while 0.080 ml of pyridine (1 mEq) and then 0.176 ml of pentafluorophenyl trifluoroacetate (1 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

6.12 grams of the product with the desired titer are obtained. Quantitative analysis of the percentage of esterification was performed by gas chromatography to determine the pentafluorophenol content after alkaline hydrolysis of the ester.

EXAMPLE 3

Preparation of a pentafluorophenyl partial ester of hyaluronic acid tetrabutylammonium salt —25% of the carboxy groups are involved in the formation of the active ester—75% of the carboxy groups are in the form of tetrabutylammonium salt 6.2 grams of hyaluronic acid tetrabutylammonium salt with a molecular weight of 120,000 Daltons, corresponding to 10 mEq of a monomeric unit, are solubilized in 310 ml of N-methylpyrrolidone at 25° C. This solution is shaken while 0.200 ml of pyridine (2.5 mEq) and then 0.440 ml of pentafluorophenyl trifluoroacetate (2.5 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

6.01 gr of the product with the desired titer are thus obtained. Quantitative analysis of the percentage of esterification was performed by gas chromatography to determine the pentafluorophenol content after alkaline hydrolysis of the ester.

EXAMPLE 4

Preparation of a pentafluorophenyl partial ester of hyaluronic acid tetrabutylammonium salt —50% of the carboxy groups are involved in the formation of the active ester—50% of the carboxy groups are in the form of tetrabutylammonium salt 6.2 grams of hyaluronic acid tetrabutylammonium salt with a molecular weight of 80,000 Daltons, corresponding to 10 mEq of a monomeric unit, are solubilized in 310 ml of N-methylpyrrolidone at 25° C. This solution is shaken while 0.400 ml of pyridine (5 mEq) and then 0.880 ml of pentafluoophenyl trifluoroacetate (5 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C. 5.82 grams of the product with the desired titer are obtained. Quantitative analysis of the percentage of esterification was performed by gas chromatography to determine the pentafluorophenol content after alkaline hydrolysis of the ester.

EXAMPLE 5

Preparation of a pentafluorophenyl partial ester of hyaluronic acid tetrabutylammonium salt —75% of the carboxy groups are involved in the formation of the active ester—25% of the carboxy groups are in the form of tetrabutylammonium salt 6.2 grams of hyaluronic acid tetrabutylammonium salt with a molecular weight of 400,000 Daltons, corresponding to 10 mEq of a monomeric unit, are solubilized in 310 ml of N-methylpyrrolidone at 25° C. This solution is shaken while 0.600 ml of pyridine (7.5 mEq) and then 1.32 ml of pentafluorophenyl trifluoroacetate (7.5 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

5.62 grams of the product with the desired titer are obtained. Quantitative analysis of the percentage of esterification was performed by gas chromatography to determine the pentafluorophenol content after alkaline hydrolysis of the ester.

EXAMPLE 6

Preparation of the pentafluorophenyl total ester of hyaluronic acid—100% of the carboxy groups are involved in the formation of the active ester 6.2 grams of hyaluronic acid tetrabutylammonium salt with a molecular weight of 180,000 Daltons, corresponding to 10 mEq of a monomeric unit, are solubilized in 310 ml of N-methylpyrrolidone at 25° C. This solution is shaken while 0.800 ml of pyridine (10 mEq) and then 1.760 ml of pentafluorophenyl trifluoroacetate (10 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

5.44 grams of the product with the desired titer are obtained. Quantitative analysis of the percentage of esterification was performed by gas chromatography to determine the pentafluorophenol content after alkaline hydrolysis of the ester.

EXAMPLE 7

Preparation of a 4-nitrophenyl partial ester of hyaluronic acid tetrabutylammonium salt —25% of the carboxy groups are involved in the formation of the active ester—75% of the carboxy groups are in the form of tetrabutylammonium salt 6.2 grams of hyaluronic acid tetrabutylammonium salt with a molecular weight of 120,000 Daltons, corresponding to 10 mEq of a monomeric unit, are solubilized in 310 ml of dimethylsulfoxide at 25° C. This solution is shaken while 0.200 ml of pyridine (2.5 mEq) and then 0.59 ml of 4-nitrophenyl trifluoroacetate solubilized in 1 ml of dimethylsulfoxide (2.5 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

5.8 grams of the product with the desired titer are thus obtained. Quantitative analysis of the percentage of esterification was performed by liquid chromatography to determine the 4-nitrophenol content after alkaline hydrolysis of the ester.

EXAMPLE 8

Preparation of a partial ester of hyaluronic acid tetrabutylammonium salt with 4-hydroxy-2,5-diphenyl-3(2H)-thiophenone-1,1-dioxide —50% of the carboxy groups are involved in the formation of the active ester—50% of the carboxy groups are in the form of tetrabutylammonium salt 6.2 grams of hyaluronic acid tetrabutylammonium salt with a molecular weight of 800,000 Daltons, corresponding to 10 mEq of a monomeric unit, are solubilized in 310 ml of N-methylsulfoxide at 25° C. This solution is shaken while 1.63 grams of 4,6-diphenylthiene- [3,4-d]-1,3-dioxol-2-one 5,5-dioxide (Steglich's reagent) solubilized in 5 ml of dimethylsulfoxide (5 mEq) are added to it. The reaction mixture is shaken at 25° C. for 30 minutes, after which the product is precipitated by the addition of 2 liters of ethyl acetate. The precipitate is filtered and washed twice with 500 ml of ethyl acetate, and then vacuum-dried for 24 hours at 30° C.

6.39 grams of the product with the desired titer are thus obtained. Quantitative analysis of the percentage of esterification was performed by liquid chromatography to determine the 4-hydroxy-2,5-diphenyl-3 (2H) -thiophenone-1,1-dioxide content after alkaline hydrolysis of the ester.

EXAMPLE 9

Preparation of a pentafluorophenyl partial ester of alcinic acid tetrabutylammonium salt —20% of the carboxy groups are involved in the formation of the active ester —80% of the carboxy groups are in the form of tetrabutylammonium salt 4.17 grams of alginic acid tetrabutylammonium salt with a molecular weight of 100,000 Daltons, corresponding to 10 mEq of a monomeric unit, are solubilized in 210 ml of N-methylpyrrolidone at 25° C. This solution is shaken while 0.160 ml of pyridine (2 mEq) and then 0.352 ml of pentafluorophenyl trifluoroacetate (2 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

4.04 grams of the product with the desired titer are thus obtained. Quantitative analysis of the percentage of esterification was performed by gas chromatography to determine the pentafluorophenol content after alkaline hydrolysis of the ester.

EXAMPLE 10

Preparation of a pentafluorophenyl partial ester of HYAFF 7p50 (50% ethyl ester of hyaluronic acid) tetrabutylammonium salt—25% of the carboxy groups are involved in the formation of the active ester—50% of the carboxy groups are esterified with ethanol—25% of the carboxy groups are in the form of tetrabutylammonium salt 5.2 grams of HYAFF 7p50 tetrabutylammonium salt with a molecular weight of 170,000 Daltons, corresponding to 10 mEq of a monomeric unit, are solubilized in 260 ml of N-methylpyrrolidone at 25° C. This solution is shaken while 0.200 ml of pyridine (2.5 mEq) and then 0.440 ml of pentafluorophenyl trifluoroacetate (2.5 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

5 grams of the product with the desired titer are thus obtained. Quantitative analysis of the percentage of esterification was performed by gas chromatography to determine the pentafluorophenol content after alkaline hydrolysis of the ester.

EXAMPLE 11

Preparation of a pentafluorophenyl ester of HYAFF 11p75 (75% benzyl ester of hyaluronic acid) tetrabutylammonium salt—25% of the carboxy groups are involved in the formation of the active ester—75% of the carboxy groups are esterified with benzyl alcohol 5.07 grams of HYAFF 11p75 tetrabutylammonium salt with a molecular weight of 120,000 Daltons, corresponding to 10 mEq of a monomeric unit, are solubilized in 260 ml of N-methylpyrrolidone at 25° C. This solution is shaken while 0.200 ml of pyridine (2.5 mEq) and then 0.440 ml of pentafluorophenyl trifluoroacetate (2.5 mEq) are added to it. The reaction mixture is shaken at 25° C. for 1 hour, after which the product is precipitated by the addition of 2 liters of ethyl acetate. The precipitate is filtered and washed twice with 500 ml of ethyl acetate, and then vacuum-dried for 24 hours at 30° C.

4.8 grams of the product with the desired titer are thus obtained. Quantitative analysis of the percentage of esterification was performed by gas chromatography to determine the pentafluorophenol content after alkaline hydrolysis of the ester.

EXAMPLE 12

Preparation of the N-ethyl partial amide of hyaluronic acid sodium salt —10% of the carboxy functions are transformed into N-ethyl amides—90% of the carboxy functions are salified with sodium 6.13 grams of the active ester obtained according to Example 2, corresponding to 10 mEq of a monomeric unit, are solubilized in 305 ml of N-methylpyrrolidone at 25° C. This solution is shaken while 66 μl of ethylamine (1 mEq) are added to it. The reaction mixture is shaken for 2 hours, after which 00 ml of a 2% solution of sodium chloride in deionized water are added to it. The addition of 800 ml of acetone to this reaction mixture causes the formation of a precipitate which is filtered and washed three times with 100 ml of acetone/water 5:1, three times with 100 ml of acetone, and which is lastly vacuum-dried for 24 hours at 30° C. 4.0 grams of the desired product are thus obtained. Quantitative analysis of the amide groups was performed to determine the ethylamine content after alkaline hydrolysis.

EXAMPLE 13

Preparation of the partial N-benzyl amide of hyaluronic acid sodium salt —50% of the carboxy functions are transformed into N-benzyl amides—50% of the carboxy functions are salified with sodium 5.83 grams of the active ester obtained according to Example 4, corresponding to 10 mEq of a monomeric unit, are solubilized in 290 ml of N-methylpyrrolidone at 25° C. This solution is shaken while 5.46 ml of benzylamine (5 mEq) are added to it. The reaction mixture is shaken for 2 hours, after which 100 ml of a 2% solution of sodium chloride in deionized water are added to it. The addition of 800 ml of acetone to this reaction mixture causes the formation of a precipitate which is filtered and washed three times with 100 ml of acetone/water 5:1, three times with 100 ml of acetone, and which is lastly vacuum-dried for 24 hours at 30° C.

4.3 grams of the desired product are thus obtained. Quantitative analysis of the amide groups was performed to determine the benzylamine content after alkaline hydrolysis.

EXAMPLE 14

Synthesis of an amide derivative of hyaluronic acid with arpinine—100% of the carboxy functions are transformed into amides of hyaluronic acid with arginine 5.45 grams of the active ester obtained according to Example 6, corresponding to 10 mEq of a monomeric unit, are solubilized in 270 ml of N-methyl pyrrolidone at 25° C. This solution is shaken while 1.74 gr of D-arginine (10 mEq) solubilized in 10 ml of N-methyl pyrrolidone are added to it. This solution is shaken for 2 hours, after which 800 ml of acetone are added to it. This causes the formation of a precipitate which is filtered, washed three times with 100 ml of acetone, and then vacuum dried for 24 hours at 30° C.

5.35 grams of the desired product are thus obtained. Quantitative analysis of the amide groups is performed to determine the arginine content after acid hydrolysis in 6N hydrochloric acid (amino acid analysis).

EXAMPLE 15

Synthesis of a derivative of HYAFF 7p50 (50% ethyl ester of hyaluronic acid) containing a peptide having the sequence H--Ara-Gly-Asp-OH —50% of the carboxy functions are esterified with ethanol—25% of the carboxy functions are transformed into amides of hyaluronic acid with the peptide—25% of the carboxy functions are salified with sodium The tripeptide known as RGD (arginine-glycine-aspartic acid) is the minimal cell-recognizable sequence in many adhesive plasma and extracellular matrix proteins. For example, the RGD tripeptide sequence has been found in vitronectin, fibronectin, von Willebrand factor, fibrinogen and collagens, and this tripeptide has been shown to play a crucial role in mediating cell attachment and subsequent cell spreading.

RGD-containing peptides are therefore of interest in the development of novel biomaterials that may improve long-term endothelial cell attachment and growth.

4.95 grams of the active ester obtained according to Example 10, corresponding to 10 mEq of a monomeric unit, are solubilized in 250 ml of N-methyl pyrrolidone at 25° C. This solution is shaken while 1.08 gr of a peptide having the sequence H-Arg-Gly-Asp-OH (2.5 mEq) solubilized in 10 ml of N-methyl pyrrolidone are added to it. This solution is shaken for 2 hours, after which 100 ml of a 2% solution of sodium chloride in deionized water are added to it. The addition of 800 ml of acetone to this reaction mixture causes the formation of a precipitate which is filtered, washed three times with 100 ml of acetone/water 5:1, three times with 100 ml of acetone, and which is then vacuum-dried for 24 hours at 30° C.

4.8 grams of the desired product are thus obtained. Quantitative determination of the amide groups is performed analysing the amino acid content.

EXAMPLE 16

Synthesis of a derivative of HYAFF 11p75 (75% benzyl ester of hyaluronic acid) containing a peptide having the sequence H-Gly-Pro-Ara-OH —75% of the carboxy functions are esterified with benzyl alcohol—25% of the carboxy functions are transformed into amides of hyaluronic acid with the peptide 4.8 grams of the active ester obtained according to Example 11, corresponding to 10 mEq of a monomeric unit, are solubilized in 240 ml of N-methyl pyrrolidone at 25° C. This solution is shaken while 0.82 grams of the peptide having the sequence H-Gly-Pro-Arg-OH (2.5 mEq) solubilized in 5 ml of N-methyl pyrrolidone are added to it. This solution is shaken for 2 hours, after which 100 ml of a 2% solution of sodium chloride in deionized water are added to it. The addition of 800 ml of acetone to this reaction mixture causes the formation of a precipitate which is filtered, washed three times with 100 ml of acetone/water 5:1, three times with 100 ml of acetone, and which is then vacuum-dried for 24 hours at 30° C.

5.2 grams of the desired product are thus obtained. Quantitative determination of the amide groups is performed analysing the amino acid content.

EXAMPLE 17

Preparation of a spongy material made with the HYAFF 7P50 (50% ethyl ester of hyaluronic acid) containing a peptide having the sequence H-Arc-Gly-Asp-OH 4 grams of the derivative of HYAFF 7p50 containing a peptide having the sequence H-Arg-Gly-Asp-OH (described in Example 15) are solubilized in 120 ml of dimethylsulfoxide. The solution is filtered and poured onto a 3×4 cm steel dish. The dish is placed in a controlled environment at 25° C. saturated with water vapour, which acts as a coagulant. A gelatinous slab is thus obtained which is cut into pieces measuring 1×1 cm.

These pieces are immersed in 2 liters of a 5% aqueous solution of NaCl. This material is freeze-dried, producing a spongy material which is then washed three times with 1 liter of distilled water to eliminate the sodium chloride incorporated in it. Pieces of spongy material measuring 0.9×0.9 cm and 4 mm thick are thus obtained.

EXAMPLE 18

Preparation of microspheres produced from HYAFF 11P75 (75% benzyl ester of hyaluronic acid) containing a peptide having the sequence H-Gly-Pro-Arg-OH, described in Example 16

The derivative of HYAFF 11p75 containing the peptide having the sequence H-Gly-Pro-Arg-OH, described in Example 16, is solubilized in 50 ml of dimethylsulfoxide at a concentration of 7% (w/v). 800 ml of a mixture of highly viscous mineral oil containing ARLACEL, a non-ionic surfactant, at a concentration of 1% (w/v), is prepared separately. The latter mixture is shaken while the HYAFF 11p75 peptide derivative-containing solution is added to it. An emulsion is formed, to which 2.5 liters of ethyl acetate are added. The ethyl acetate mixes with the emulsion phase, but the peptide derivative is insoluble in it. The suspension thus obtained is filtered, and the resulting microspheres are washed with 6 liters of N-hexane. The mean particle size of the microspheres is 15 μm.

EXAMPLE 19

Preparation of the partial N-propyl amide of hyaluronic acid sodium salt—50% of the carboxy functions are transformed into N-propyl amide—50% of the carboxy functions are salified with sodium 5.83 grams of the active ester obtained as in Example 4 corresponding to 10 mEq of a monomeric unit are solubilized in 290 ml of N-methylpyrrolidone at 25° C. To this solution are added, while stirring, 0.41 ml of N-propylamine (5 mEq). The mixture is stirred for 2 hours and then 100 ml of a 2% solution of sodium chloride in deionized water are added. The addition to this reaction mixture of 800 ml of acetone causes the formation of a precipitate, which is filtered and washed three times with 100 ml of acetone and then vacuum-dried for 24 hours at 30° C.

4.2 grams of the desired product are thus obtained. Quantitative determination of the amide groups is performed by analysing the N-propylamine content after alkaline hydrolysis.

EXAMPLE 20

Preparation of an amide derivative of hyaluronic acid with glycine—50% of the carboxy functions are transformed into glycinamides—50% of the carboxy functions are salified with sodium 5.83 grams of the active ester obtained as in Example 4 corresponding to 10 mEq of a monomeric unit are solubilized in 290 ml of N-methylpyrrolidone at 25° C. To this solution are added, with stirring, 0.375 grams of glycine. The mixture is stirred for 2 hours and then 100 ml of a 2i solution of sodium chloride in deionized water are added. The addition to this reaction mixture of 800 ml of acetone causes the formation of a precipitate, which is filtered and washed three times with 100 ml of acetone and then vacuum-dried for 24 hours at 30° C.

4.3 grams of the desired product are thus obtained. Quantitative determination of the amide groups is performed by analysing the glycine content after acid hydrolysis in 6N hydrochloric acid (amino acid analysis).

EXAMPLE 21

Preparation of an amide derivative of hyaluronic acid with lysine—100% of the carboxy functions are transformed into hyaluronic acid amides with lysine 5.45 grams of the active ester obtained as in Example 6 corresponding to 10 mEq of a monomeric unit are solubilized in 270 ml of N-methylpyrrolidone at 25° C. To this solution are added, with stirring, 1.46 grams of lysine. The mixture is stirred for 2 hours and then 100 ml of a 2% solution of sodium chloride in deionized water are added. The addition to this reaction mixture of 800 ml of acetone causes the formation of a precipitate, which is filtered and washed three times with 100 ml of acetone and then vacuum-dried for 24 hours at 30° C.

5.0 grams of the desired product are thus obtained. Quantitative determination of the amide groups is performed by analysing the lysine content after acid hydrolysis in 6N hydrochloric acid (amino acid analysis).

EXAMPLE 22

Preparation of an amide derivative of hyaluronic acid with serine benzyl ester—10% of the carboxy functions are transformed into hyaluronic acid amides with serine benzyl ester—90% of the carboxy functions are salified with sodium 6.13 grams of the active ester obtained as in Example 2 corresponding to 10 mEq of a monomeric unit are solubilized in 305 ml of N-methylpyrrolidone at 25° C. To this solution are added, with stirring, 0.194 grams of serine benzyl ester. The mixture is stirred for 2 hours and then 100 ml of a 2% solution of sodium chloride in deionized water are added. The addition to this reaction mixture of 800 ml of acetone causes the formation of a precipitate, which is filtered and washed three times with 100 ml of acetone and then vacuum-dried for 24 hours at 30° C.

4.5 grams of the desired product are thus obtained. Quantitative determination of the amide groups is performed by analysing the serine content after acid hydrolysis in 6N hydrochloric acid (amino acid analysis).

EXAMPLE 23

Synthesis of a peptide derivative of hyaluronic acid containing a peptide having the sequence Phe-Val-Glu-Tyr-Leu (SEQ ID NO:1) —50% of the carboxy functions are tranformed into amides of hyaluronic acid with the peptide—50% of the carboxy functions are salified with sodium 5.83 grams of the active ester obtained as in Example 2 corresponding to 10 mEq of a monomeric unit are solubilized in 290 ml of N-methylpyrrolidone at 25° C. To this solution are added, with stirring, 3.46 grams of a peptide having the sequence Phe-Val-Glu-Tyr-Leu (SEQ ID NO:1) (5 mEq) solubilized in 20 ml of N-methylpyrrolidone. The mixture is stirred for 2 hours and then 100 ml of a 20% solution of sodium chloride in deionized water are added. The addition to this reaction mixture of 800 ml of acetone causes the formation of a precipitate, which is filtered and washed three times with 100 ml of acetone and then vacuum-dried for 24 hours at 30° C.

5.4 grams of the desired product are thus obtained. Quantitative determination of the amide groups is performed by analysing the amino acid content after acid hydrolysis in 6N hydrochloric acid (amino acid analysis).

EXAMPLE 24

Synthesis of a peptide derivative of HYAFF 11p75 containing a peptide having the sequence Gly-Arg-Gly-A- Ser-Tyr (SEQ ID NO:2) —25% of the carboxy functions are transformed into amides of hyaluronic acid with the peptide—75% of the carboxy functions are esterified with benzyl alcohol 4.8 grams of the active ester obtained as in Example 11 corresponding to 10 mEq of a monomeric unit are solubilized in 240 ml of N-methylpyrrolidone at 25° C. To this solution are added, with stirring, 1.85 grams of a peptide having the sequence Gly-Arg-Gly-Asp-Ser-Tyr (SEQ ID NO:2) (2.5 mEq) solubilized in 10 ml of N-methylpyrrolidone. The mixture is stirred for 2 hours and then 100 ml of a 2% solution of sodium chloride in deionized water are added. The addition to this reaction mixture of 800 ml of acetone causes the formation of a precipitate, which is filtered and washed three times with 100 ml of acetone and then vacuum-dried for 24 hours at 30° C.

5.0 grams of the desired product are thus obtained. Quantitative determination of the amide groups is performed by analysing the amino acid content after acid hydrolysis in 6N hydrochloric acid (amino acid analysis).

EXAMPLE 25

Synthesis of a peptide derivative of HYAFF 7p50 containing a peptide having the sequence Gly-Arg-Gly-Asp-Val-Tyr (SEQ ID NO:3) —50% of the carboxy functions are transformed into amides of hyaluronic acid with the peptide —50% of the carboxy functions are esterified with ethyl alcohol 4.95 grams of the active ester obtained as in Example 10 corresponding to 10 mEq of a monomeric unit are solubilized in 250 ml of N-methylpyrrolidone at 25° C. To this solution are added, with stirring, 3.765 grams of a peptide having the sequence Gly-Arg-Gly-Asp-Val-Tyr (SEQ ID NO:3) (5 mEq) solubilized in 20 ml of N-methylpyrrolidone. The mixture is stirred for 2 hours and then 100 ml of a 2% solution of sodium chloride in deionized water are added. The addition to this reaction mixture of 800 ml of acetone causes the formation of a precipitate, which is filtered and washed three times with 100 ml of acetone and then vacuum-dried for 24 hours at 30° C.

5.1 grams of the desired product are thus obtained. Quantitative determination of the amide groups is performed by analysing the amino acid content after acid hydrolysis in 6N hydrochloric acid (amino acid analysis).

EXAMPLE 26

Preparation of a partial thiofuran thioester of hyaluronic acid sodium salt—10% of the carboxy groups are involved in the formation of the thioester —90% of the carboxy groups are salified with sodium 6.13 grams of the active ester obtained as in Example 2 corresponding to 10 mEq of a monomeric unit are solubilized in 305 ml of N-methylpyrrolidone at 25° C. To this solution are added, with stirring, 79.4 ml of thiofuran. The mixture is stirred for 2 hours and then 100 ml of a 2% solution of sodium chloride in deionized water is added. The addition to this reaction mixture of 800 ml of acetone causes the formation of a precipitate, which is filtered and washed three times with 100 ml of acetone and then vacuum-dried for 24 hours at 30° C.

6.3 grams of the desired product are thus obtained. Quantitative determination of the amide groups is performed by analysing the thiofuran content after basic hydrolysis.

EXAMPLE 27

Sponges

One gram of the heptyl amide of HA with a molecular weight of 200 Kda, wherein the carboxy groups are employed in the substitution reaction, are dissolved in 10 ml of dimethylsulfoxide. The solution is homogenized to form a mixture containing 30 grams of NaCl, 1.3 grams of bicarbonate of soda and 1 gram of citric acid.

Once the final mixture is completely homogenized, it is passed between two rollers placed at a suitable distance from one another and turning in opposite directions. A layer of material is obtained by passing the mixture between them on a silicone support. The layer is then cut to the desired dimensions and the silicone support is removed. The layer is washed thoroughly with water and dried. It can then be sterilized with gamma rays.

EXAMPLE 28

Films

A solution is prepared by solubilizing the N-benzyl amide of HA in dimethylsulfoxide at a concentration of 180 mg/ml.

By means of a stratifier, a thin layer of solution is spread on a glass sheet; the thickness must be 10 times greater than the final thickness of the film. The glass sheet is immersed in ethanol, which absorbs the dimethylsulfoxide, but which does not solubilize the HA N-benzyl amide, which becomes solid. The film is detached from the glass sheet, repeatedly washed with ethanol, then with water, and then again with ethanol.

The resulting sheet is dried in a press for 48 hours at 30° C.

The invention being thus described, it is obvious that the same can be modified in various ways. Such modifications are not to be considered as departures from the spirit and scope of the present invention, and any modifications that would appear obvious to one skilled in the art are to be considered as coming within the scope of the following claims.

---

What is claimed is:

1. An isolated active ester of a carboxy polysaccharide or active ester of a semisynthetic derivative of a carboxy polysaccharide,
   wherein all or part of the carboxy groups thereof are actively esterified with an alcohol selected from the group consisting of an aromatic alcohol, a substituted aromatic alcohol, an aromatic heterocyclic alcohol, a substituted aromatic heterocyclic alcohol, an N-hydroxylamine, and a combination thereof,
   wherein when only part of the carboxy groups of said carboxy polysaccharide or said semisynthetic derivative of said carboxy polysaccharide are actively esterified, the remaining carboxy groups are salified with a member selected from the group consisting of a quaternary ammonium salt, an alkaline metal, an alkaline earth metal, and a combination thereof.

2. The active ester according to claim 1, wherein said alcohol is an aromatic alcohol.

3. The active ester according to claim 2, wherein said aromatic alcohol is a substituted aromatic alcohol.

4. The active ester according to claim 3, wherein said substituted aromatic alcohol is selected from the group consisting of a fluoro-substituted aromatic alcohol, a chloro substituted aromatic alcohol, and a nitro-substituted aromatic alcohol.

5. The active ester according to claim 4, wherein said substituted aromatic alcohol is selected from the group consisting of pentafluorophenol, pentachlorophenol, 4-nitrophenol, and a combination thereof.

6. The active ester according to claim 1, wherein said alcohol is an aromatic heterocyclic alcohol.

7. The active ester according to claim 6, wherein said aromatic heterocyclic alcohol is selected from the group consisting of a benzotriazoline alcohol, a thiophene alcohol, a hydroxypyridine alcohol, a pyrazoline alcohol, and a combination thereof.

8. The active ester according to claim 6, wherein said aromatic heterocyclic alcohol is selected from the group consisting of 2-hydroxypyridine, 3-hydroxypyridine, 3,4-dihydro-4-oxobenzotrizine-3-ol, 4-hydroxy-2,5-diphenyl-3(2H)thiophenone-1,1-dioxide, 3-phenyl-1-(p-nitrophenyl)-2-pyrazoline-5-one, 3-methyl-1-(p-nitrophenyl)-2-pyrazoline-5-one, and a combination thereof.

9. The active ester according to claim 1, wherein said alcohol is an N-hydroxylamine.

10. The active ester according to claim 9, wherein said N-hydroxylamine is selected from the group consisting of N-hydroxysuccinimide, N-hydroxyphthalimide, and a combination thereof.

11. The active ester according to claim 1, wherein said quaternary ammonium salt is a tetraalkylammonium salt.

12. The active ester according to claim 11, wherein said tetraalkylammonium salt is a tetrabutylammonium salt.

13. The active ester according to claim 1, wherein said carboxy polysaccharide or semisynthetic derivative thereof is selected from the group consisting of a glycosaminoglycan, alginic acid, gellan, carboxymethylcellulose, carboxymethylchitin, and a partial ester thereof.

14. The active ester according to claim 1, wherein said glycosaminoglycan is hyaluronic acid.

15. The active ester according to claim 1, wherein said active ester is synthesized from a tetrabutylammonium salt selected from the group consisting of the tetrabutylammonium salt of a glycosaminoglycan, the tetrabutylammonium salt of alginic acid, the tetrabutylammonium salt of gellan, the tetrabutylammonium salt of carboxymethylcellulose, and the tetrabutylammonium salt of carboxymethylchitin.

16. The active ester according to claim 1, wherein said semisynthetic derivative of said carboxy polysaccharide is a partial ester of said carboxy polysaccharide.

17. The active ester according to claim 16, wherein said partial ester is an ester with an alcohol selected from the group consisting of an aliphatic alcohol, an araliphatic alcohol, a cycloaliphatic alcohol, a heterocyclic alcohol, and a combination thereof.

18. The active ester according to claim 17, wherein said aliphatic alcohol contains between 2 and 34 carbon atoms.

19. The active ester according to claim 17, wherein said partial ester is an ester with ethyl alcohol.

20. The active ester according to claim 17, wherein said partial ester is an ester with an araliphatic alcohol.

21. The active ester according to claim 20, wherein said araliphatic alcohol is benzyl alcohol.

22. An active ester according to claim 1, selected from the group consisting of a pentafluorophenyl ester of hyaluronic acid with 5% of its carboxy groups involved in the formation of the active ester and wherein the remaining 95% of the carboxy groups are salified with tetrabutylammonium; a pentafluorophenyl ester of hyaluronic acid with 10% of its carboxy groups involved in the formation of the active ester and wherein the remaining 90% of the carboxy groups are salified with tetrabutylammonium; a pentafluorophenyl ester of hyaluronic acid with 25% of its carboxy groups involved in the formation of the active ester and wherein the remaining 75% of the carboxy group are salified with tetrabutylammonium; a pentafluorophenyl ester of hyaluronic acid with 50% of its carboxy groups involved in the formation of the active ester and wherein the remaining 50% of the carboxy groups are salified with tetrabutylammonium; a pentafluorophenyl ester of hyaluronic acid with 75% of its carboxy groups involved in the formation of the active ester and wherein the remaining 25% of the carboxy groups are salified with tetrabutylammonium; a pentafluorophenyl ester of hyaluronic acid with 100% of its carboxy groups involved n the formation of the active ester; a 4-nitrophenyl ester of hyaluronic acid with 25% of its carboxy groups involved in the formation of the active ester and wherein the remaining 75% of the carboxy groups are salified with tetrabutylammonium; a 2,5-diphenyl-thiophene-4-yl-3(2H)-one 1,1-dioxide ester of hyaluronic acid with 50% of its carboxy groups involved in the formation of the active ester and wherein the remaining 50% of the carboxy groups are salified with tetrabutylammonium, a pentafluorophenyl ester of alginic acid with 20% of its carboxy groups involved in the formation of the active ester and wherein the remaining 80% of the carboxy groups are salified with tetrabutylammonium; a pentafluorophenyl ester of the ethyl ester of hyaluronic acid p50 with 25% of its carboxy groups involved in the formation of the active ester and wherein 50% of the carboxy groups are esterified with ethanol and the remaining 25% of the carboxy groups are salified with tetrabutylammonium; and a pentafluorophenyl ester of the benzyl ester of hyaluronic acid p75 wherein 25% of the carboxy groups are involved in the formation of the active ester and the remaining 75% of the carboxy groups are esterified with benzyl alcohol.

23. A process for producing an active ester according to claim 1, comprising reacting a tetraalkylammonium said of said carboxy polysaccharide or said semisynthetic derivative of said carboxy polysaccharide with a reactive alcohol to be bound to the carboxyl groups thereof in an aprotic solvent at a temperature of between about 0° and about 60° C.

24. The process according to claim 23, wherein said reactive alcohol is selected from the group consisting of a trifluoroacetate, a carbonate, an oxalate, a sulfite, and a phosphite of said alcohol.

25. The process according to claim 23, wherein said reactive alcohol is a member selected from the group consisting of a 4-nitrophenyl trifluoracetate, pentafluorophenyl trifluoroacetate, di-pentafluorophenyl sulfite, di-(N-succinimidyl) carbonate and 4,6-diphenylthiene(3,4-d)-1,3-dioxol-2-one 5,5 dioxide.

26. The process according to claim 23, wherein said aprotic solvent is selected from the group consisting of dimethylsulfoxide, N-methylpyrrolidone, and N,N-dimethylformamide.

27. The process according to claim 23, wherein said tetraalkylammonium salt is a tetrabutylammonium salt.

28. A method of producing a a modified carboxy polysaccharide or a modified semisynthetic derivative of a carboxy polysaccharide comprising reacting an active ester of claim 1, with a member selected from the group consisting of an amine, an amino acid, a peptide and a protein.

29. The method of claim 28, wherein said modified carboxy polysaccharide or said modified semisynthetic derivative of a carboxy polysaccharide is an ester, thioester, or amide.

30. The method of claim 28, wherein said amine is selected from the group consisting of a primary amine, an aliphatic amine, an araliphatic amine, a substituted aliphatic amine, and a substituted araliphatic amine.

31. The method of claim 28 wherein said amino acid, peptide, or protein is biologically active.

32. The method of claim 28 further comprising reacting said active ester with said amine, said amino acid, said peptide, or said protein in an aprotic solvent at a temperature of between about 0° and 60° C.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:1:

Phe    Val    Glu    Tyr    Leu
    1                                5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:2:

Gly    Arg    Gly    Asp    Ser    Tyr
    1                                5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:3:

Gly    Arg    Gly    Asp    Val    Tyr
    1                                5

( 2 ) INFORMATION FOR SEQ ID NO:4:

(i) SEQUENCE CHARACTERISTICS:
    (A) LENGTH: 6 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:4:

Gly  Arg  Gly  Glu  Ser  Tyr
 1                     5